(12) United States Patent
Fujiyama

(10) Patent No.: US 6,559,940 B2
(45) Date of Patent: May 6, 2003

(54) MEASURING CELL

(75) Inventor: Yoichi Fujiyama, Nara (JP)

(73) Assignee: Shimadzu Corporation, Kyoto (JP)

( * ) Notice: Subject to any disclaimer, the term of this patent is extended or adjusted under 35 U.S.C. 154(b) by 224 days.

(21) Appl. No.: 09/748,170

(22) Filed: Dec. 27, 2000

(65) Prior Publication Data
US 2001/0007497 A1 Jul. 12, 2001

(30) Foreign Application Priority Data
Jan. 11, 2000 (JP) .................................. 2000-002663

(51) Int. Cl.$^7$ ................................................ G01N 1/10
(52) U.S. Cl. ........................................................ 356/246
(58) Field of Search ................................. 356/246, 244, 356/440; 422/99

(56) References Cited

U.S. PATENT DOCUMENTS 4,643,570 A * 2/1987 Machler et al. ............. 250/576
5,304,487 A * 4/1994 Wilding et al. .......... 210/500.26
5,587,128 A * 12/1996 Wilding et al. ................. 216/2
5,876,675 A * 3/1999 Kennedy ..................... 204/451
6,030,883 A 2/2000 Nishimoto et al.

FOREIGN PATENT DOCUMENTS

EP 0 808 808 11/1997
EP 808808 A1 * 11/1997

* cited by examiner

Primary Examiner—John R. Lee
Assistant Examiner—James Leybourne
(74) Attorney, Agent, or Firm—Kanesaka & Takeuchi

(57) ABSTRACT

A measuring cell is formed of base plates joined together. A passage groove is formed on a joining surface of one base plate. Through-holes for introducing and discharging a fluid sample are formed on the other base plate, and the joining surface is provided with an optically opaque Si film as slits. Further, the joining surfaces of the base plates and the inner surface of the passage groove are covered with $SiO_2$ films. Thus, a measuring cell having a sufficiently small passage sectional area, a high air-tightness, a chemically stable measuring chamber, and a high measuring sensitivity can be obtained.

4 Claims, 2 Drawing Sheets

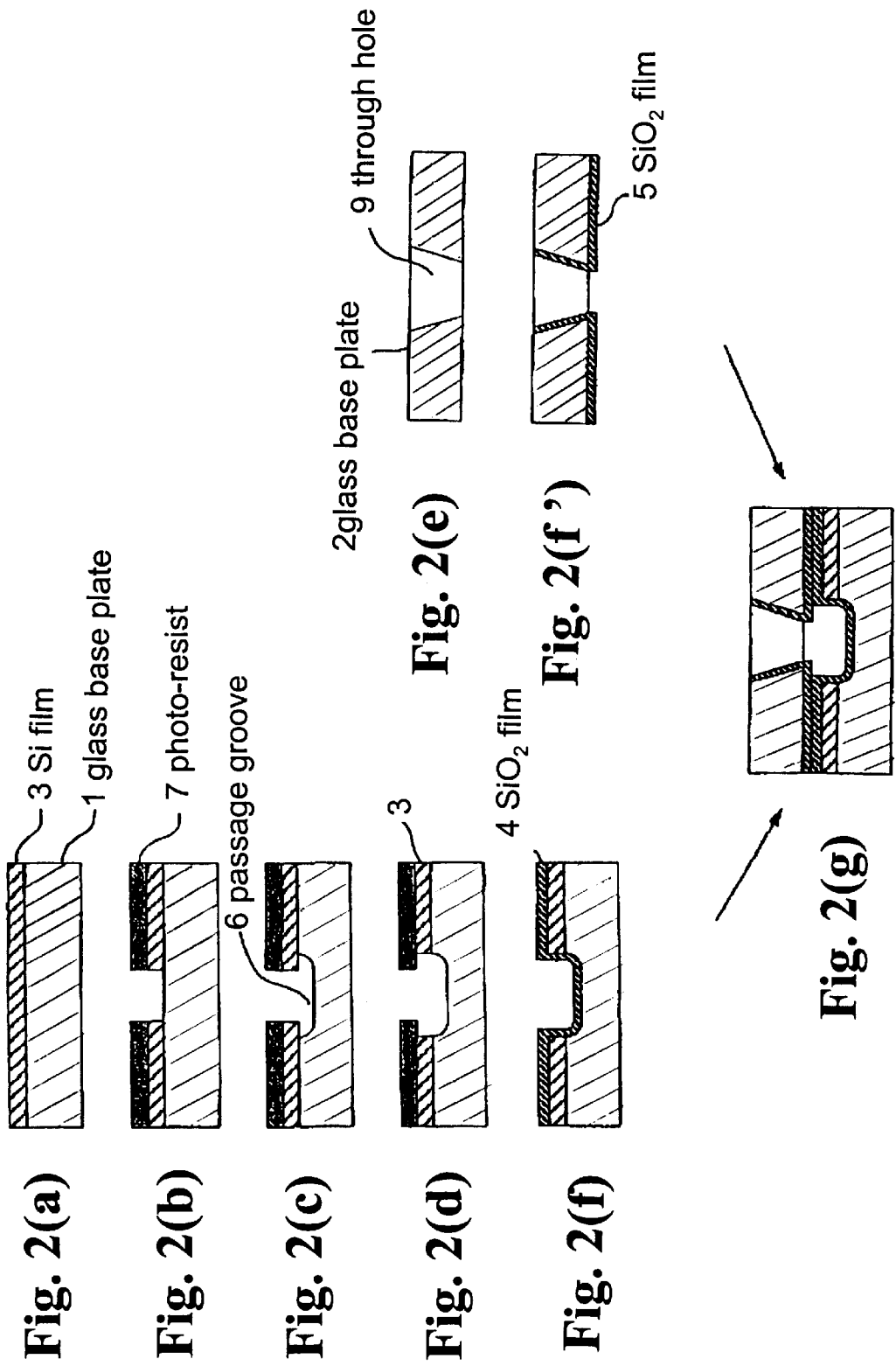

MEASURING CELL

BACKGROUND OF THE INVENTION AND RELATED ART STATEMENT

The present invention relates to a measuring cell to be used in an optical measurement apparatus for measuring absorption or emission of rays in an ultraviolet or visible region to measure components in an extremely small quantity of a liquid sample.

A measuring cell for measuring absorption or emission of rays of a liquid sample in an ultraviolet or visible region has been widely used as a detecting device for accurately and quickly analyzing extremely small quantities of components, for example a capillary electrocataphoresis (CE), a high performance liquid chromatography (HPLC), a capillary electro chromatography (CEC), or a flow injection analysis (FIA) in a field of analytical chemistry, especially such as an environment analytical chemistry, a clinical field, a pharmaceutical field or the like. The measuring cell includes, generally, an introducing port for introducing a liquid sample to be analyzed, a passage of the liquid sample, and a discharging port for discharging the liquid sample, and the passage has a measuring chamber wherein the liquid sample and rays in an ultraviolet or visible region interact. The measuring cell is connected to an exit of an analytical column used in the analyzing apparatus. Also, the measuring chamber is provided with an incident window and an exit window of the measuring rays, and the rays in the ultraviolet or visible region introduced into the measuring chamber through the incident window pass through the liquid sample present in the measuring chamber, go out through the exit window, and are measured by a photometry optical system.

Recently, for example, as published in "Science", Vol. 261, p 895-897 (1993), there has been developed an electrocataphoresis device wherein a passage for introducing a liquid material and a passage for separating a liquid sample are formed on an electrocatahoresis member made of a glass base plate, for example PYREX GLASS, by using a micromachining technique based on a semiconductor manufacturing technique. When compared with a conventional capillary electrocataphoresis device, the electrocataphoresis device has various advantages such that a high speed analysis can be made, a solvent consuming quantity is very little, a required sample is extremely small, the device can be miniaturized, and the like. These characteristics are very useful for enabling an on-sight or bed-side analysis, which can not be made by the conventional analyzing devices in the field of analytical chemistry. Also, in a field of a DNA analysis or the like, the above-mentioned advantages are useful for screening from a view point of the high speed analysis.

In the measuring cell to be used in a field of the analytical chemistry, a volume of the measuring chamber is required such that separating or analyzing ability for the various analytical methods are not impaired, i.e. the passage sectional area is generally the same as that of a separation capillary column. As the separation capillary column, generally, a molten silica capillary having an inner diameter in the order of several hundreds $\mu$m is used. In order to obtain a measuring chamber having the same sectional area of the passage as that of the molten silica capillary, there has been proposed a manufacturing method of a measuring cell by joining two glass base plates provided with a passage on the surface thereof by applying the micro-machining technique.

In this case, it is important that the two base plates are securely joined and the surface of the passage is chemically stable in view of an influence on an analysis. However, in a conventional joining method employing a thermal oxidation film of an Si thin film, there may be formed a thermal stress and distortion on the base plates due to high temperature process to obtain the thermal oxidation film, so that the joining of the base plates becomes insecure and the measuring chamber can not be kept air-tightly.

Also, in case the measuring cell is desired to be used as a disposable cell, although a plastic cell is advantageous in view of its cost, it is required at the present situation that the two base plates are processed at a temperature higher than 100° C. in a joining process thereof. Thus, it is difficult to bond the base plates while keeping the passage shape of the accurately formed plastic base plates. Also, since the surface of the plastic product mostly show hydrophobic property, there is a problem that a solution can not be easily introduced into the cell.

Also, among incident lights entering the measuring chamber, lights, i.e. stray lights, which do not interact with a liquid sample to be measured, enter a measuring device to thereby lower a measuring sensitivity.

The present invention has been made to solve the above problems, and an object of the invention is to provide a disposable measuring cell, wherein a passage of a measuring chamber has substantially the same sectional area as that of a separation capillary column; the measuring chamber has a sufficient airtightness; the inner surface of the passage is chemically stable; and stray lights do not enter a measuring device.

Another object of the invention is to provide a measuring cell as stated above, wherein the entire measuring cell is miniaturized with high accuracy to thereby produce a plurality of measuring cells at the same time and reduce its cost.

Further objects and advantages of the invention will be apparent from the following description of the invention.

SUMMARY OF THE INVENTION

A measuring cell of the invention for attaining the above objects includes a sample introducing port for introducing a liquid sample, a passage for the introduced liquid sample, and a sample discharging port for discharging the liquid sample. At least a part of the passage is used as a measuring chamber. The measuring cell is formed of two base plates joined together by using an $SiO_2$ thin film formed by a sputtering film forming method or the like, and a groove portion as the passage is formed on a joining surface of at least one of the two base plates. Thus, without using a high thermal process step causing a thermal stress on the base plates, joining of the glass base plates can be securely carried out. Moreover, since the inner surface of the passage is covered by the $SiO_2$ thin film, a material of the base plates does not contact the liquid sample. Thus, the chemical and physical characteristics of the inner surface of the passage are determined by characteristics of the thin film formed thereto, so that various characteristics can be relatively easily provided to the inner surface of the passage by changing film forming conditions and compositions of the materials.

Also, in order to form a groove portion as the passage on a joining interface or surface of the base plate, a known photo-fabrication technique and a wet etching technique can be used to thereby form the groove portion with a desired width and depth less than several hundreds $\mu$m in either case. Therefore, a fine passage having a passage sectional area which is substantially the same as that of the separation capillary column can be used as the measuring chamber, so that it is possible to form a measuring chamber having a fine volume to an extent which does not impair separation or analyzing abilities of the various separation analyzing devices. Further, by providing optically opaque portions on both sides of the sample passage in a flow direction of the sample through formation of the optically opaque portions, such as an Si thin film, by the sputtering method on the joining surface, stray lights which do not interact with the liquid sample to be measured do not enter the measuring device, so that the measuring cell having a high measuring sensitivity can be obtained.

In case at least one of the two base plates is made of a plastic material, a cheap disposable measuring cell can be manufactured. When the plastic material is used for the base plate, although there are problems of keeping a passage shape at the time of joining the base plates and the hydrophobic property of the surfaces, the passage shape can be easily maintained and the inner surface of the passage become hydrophilic by covering the plastic surfaces with the $SiO_2$ thin films and joining the base plates by using means, such as a hydrofluoric acid joining or the like.

Incidentally, it is preferable that the thicknesses of the base plates are made thin as little as possible in order to suppress absorption of lights to be measured by the base plates, i.e. in a range from several hundreds μm to 1 mm. Although a size of the measuring cell is not specially limited, it is desirable that the measuring chamber has a length in the order of several hundreds um not to lower its resolving power.

Also, in case a liquid sample is measured through absorption of ultraviolet rays, when ultraviolet transmittance glass having a good transmittance to an ultraviolet ray region, foe example, Product No. UV-22 manufactured by Hoya Corporation or #9741 manufactured by Corning Inc., is used as base plates to provide the above structure, a measuring cell usable for measuring light absorption in the ultraviolet ray region can be obtained. When it is desired to increase the ultraviolet ray transmittance, if the above structure is embodied by using quartz glass as the base plates, an ideal measuring cell for light absorption in the ultraviolet ray region can be obtained.

BRIEF DESCRIPTION OF THE DRAWINGS

FIG. 1(*b*) is a sectional view showing a structure of the measuring cell of the embodiment according to the present invention; and FIGS. 2(*a*)–2(*g*) are sectional views showing a manufacturing process of the measuring cell shown in FIG. 1.

DETAILED DESCRIPTION OF PREFERRED EMBODIMENTS

Figure 1A:
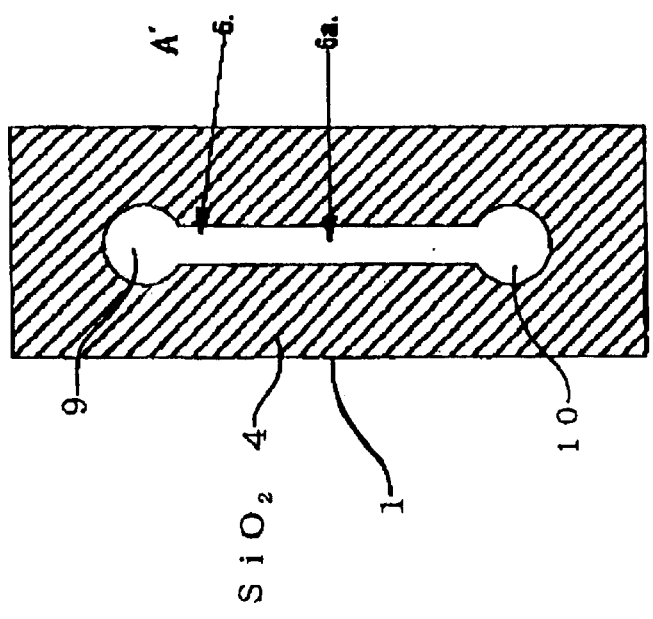
FIG. 1(*a*) is a sectional view taken along line 1(*a*)—1(*a*) in FIG. 1(*b*) showing a measuring cell of an embodiment according to the present invention.
Figure 1B:
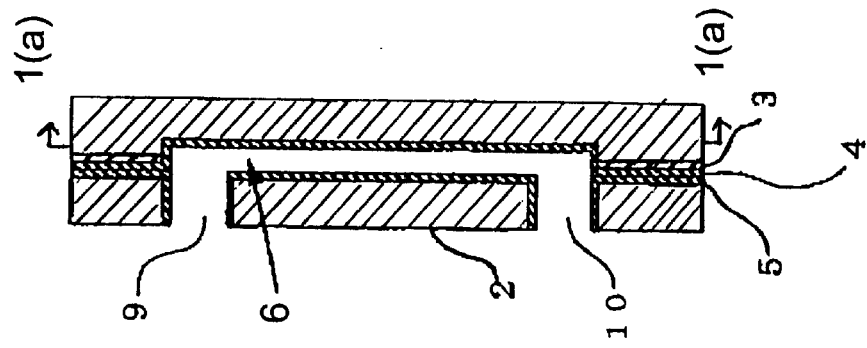

Hereinbelow, embodiments of the present invention are explained with reference to the accompanying drawings. FIGS. 1(*a*) and 1(*b*) show a structure of an embodiment of a measuring cell according to the present invention. In the drawings, reference numerals 1, 2 represent glass base plates, for example, quartz glass base plates. A fine passage groove 6 to be used as a liquid sample passage having a width and a depth less than several hundreds μformed on one surface of the glass base plate 1. Slits 3 made of, for example, an optically opaque Si film for shutting out detecting lights in an ultraviolet or visible region, and an $SiO_2$ film 4 for joining the glass base plates 1 and 2 are formed on the portion of the glass base plate 1 except for the passage groove 6 thereof. Also, only the $SiO_2$ film 4 is formed on the inner surface of the passage groove 6.

On the other hand, through-holes 9 and 10 for introducing and discharging a liquid sample are formed on the glass base plate 2. Further, the same $SiO_2$ film 5 as that formed on the inner surface of the passage groove 6 of the base plate 1 is also formed on the inner surface of a passage portion of the base plate 2 to make the characteristics of the passage inner surfaces uniform. Joining surfaces of the glass base plates 1 and 2 face each other to be closely attached and airtightly joined by a joining device using a hydrofluoric acid solution, described later, to thereby form the passage groove 6 for the liquid sample.

In the measuring cell having the structure as described above, when a portion of the fine passage groove 6 for the liquid sample is used as a measuring chamber 6*a*, the measuring chamber 6*a* having a sufficiently fine volume can be formed. Also, in case the $SiO_2$ thin film is formed on the inner surface of the passage groove 6 of the base plates 1 and 2, chemical characteristics, such as a chemical durability and a hydrophilic property, can be provided to the passage groove 6. Further, in case a measuring incident light enters the measuring cell, the measuring light passes through only the measuring chamber 6*a*, i.e. a part of the liquid sample passage groove 6, and the lights other than the measuring light are blocked by the optically opaque Si film 3 which works as slits, so that stray lights can be reduced when compared with a conventional case to improve a measuring sensitivity.

Next, a production process of the measuring cell described above is explained with reference to FIGS. 2(*a*)–2(*g*). First, as shown in FIG. 2(*a*), after a glass base plate 1 made of quartz glass is washed, an etching protective film, for example, an Si film 3, having a thickness of 3000 Å is formed by a thin film forming device, for example a sputtering film forming device. At this time, the Si film 3 functions as an etching protective film as well as the optically opaque slit. The material and film thickness of the etching protective film are not specially limited as stated above, and any optically opaque material and thickness which is tolerable for a solution to be used in a succeeding etching process can be employed.

Next, as shown in FIG. 2(*b*), the Si film 3 as the etching protective film is subjected to a photolithography for patterning thereof to thereby form a photo-resist 7. Thereafter, the silicon film is subjected to a reactive ion etching (RIE) using, for example, an $SF_6$ gas. Here, the material and the thickness of the photo-resist 7 are not specially limited, and an exposure of the photo-resist 7 can be carried out by an aligner or stepper generally used in manufacturing semiconductors. Further, a developer for developing the photo-resist 7 is not specially limited if the developer is used to develop the photo-resist to be used.

Then, as shown in FIG. 2(*c*), by using the etching protective Si film 3 and the photo-resist 7 as a mask, the quartz glass base plate 1 is subjected to etching with use of a buffered hydrofluoric acid (hereinafter referred to as "BHF") solution warmed to a temperature in the order of 37° C., for example, to thereby form the sample passage groove 6. At this time, as the etching progresses, although a passage width becomes wider than that of the patterning, if a design is made while considering this point in advance, an objective passage width can be obtained. Incidentally, the etching liquid of the quart glass base plate is not limited to the BHF solution, and any solution that can etch the quart glass without problems can be used.

Further, as shown in FIG. 2(d), after the portions extending over the sample passage groove 6 of the Si film 3 as the etching protective film are removed by the RIE, the photoresist 7 is peeled off.

On the other hand, with respect to the glass base plate 2, as shown in FIG. 2(e), through-holes 9 and 10 for introducing and discharging the liquid sample are formed, in advance, by a sand blast, for example, or the like.

Thereafter, as shown in FIGS. 2(f) and 2(f)', $SiO_2$ films 4, 5 are formed on the joining surfaces and passage inner surfaces of the base plates 1, 2 by a sputtering method. In forming the films by the sputtering method, pure $SiO_2$ is used as a target. After a sputtering reaction vessel is vacuumed, 10 ccm of an argon gas is introduced thereinto under a film forming pressure of 2 mmTorr and a power of 150 W with respect to the target having a diameter of 6 inches to thereby perform sputtering, so that the $SiO_2$ films 4, 5 having a film thickness of the order of 100 nm can be obtained.

Finally, the glass base plate 1 on which the sample passage groove 6 and the Si film 3 are formed by the processes as shown in FIGS. 2(a) to 2(d) and 2(f), and the glass base plate 2 in which the through-holes 9, 10 are formed by the processes as shown in FIGS. 2(e) and 2(f)' are laminated each other while a hydrofluoric acid aqueous solution of 0.5% is provided between the interfaces thereof. Then, while a weight of the order of 1 MPa is being loaded thereon, if necessary, the laminated structure is held for 6 hours at a temperature of 60° C. to thereby join the glass base plates 1 and 2 and obtain a measuring cell as shown in FIG. 2(g).

In the measuring cell having the structure and manufactured by the manufacturing method as described above, since a portion of the passage groove 6 having a fine width and depth formed by the photo-fabrication technique and the wet etching technique, and having the same passage sectional area as that of a separation capillary column, is used as the measuring chamber 6a, the measuring chamber having a sufficiently fine volume can be obtained. Also, in joining the two glass base plates 1, 2, the joining interfaces are covered by the $SiO_2$ films 4, 5 formed by the sputtering method, and the inner surface of the passage groove 6 is covered by the $SiO_2$ films 4, 5 so that the materials of the base plates for the inner surface of the passage groove 6 are not exposed. Thus, any distortion and thermal stress are not formed on the base plates to thereby obtain a positive joining. Further, the inner surface of the passage groove 6 is chemically stable and covered by the $SiO_2$ thin film having a hydrophilic property, so that the chemically stable measuring cell can be obtained. Also, since the optically opaque Si film 3 is formed on the joining surfaces as the slit by the sputtering method, stray lights do not enter the detecting device, and the detecting device measures only the lights which interact with the sample as signals to thereby obtain a high measuring sensitivity.

In the present embodiment, although the $SiO_2$ thin films 4, 5 are formed by the sputtering method, the film forming conditions of the $SiO_2$ thin films and the thicknesses are not specially limited, and they can be varied in view of the covering conditions and adhesiveness with respect to the base plates 1, 2. Further, the forming method of the $SiO_2$ thin film is not limited to the sputtering method, and any film forming method, which does not require a high temperature processing step with respect to the base plates 1, 2, may be used, and there are, for example, a CVD method, an evaporation method, a sol/gel method using metal alkoxide, and the like.

Also, a plastic material may be used for the base plates 1, 2. According to the present invention, the base plates 1, 2 can be joined at a temperature lower than 60° C. with the $SiO_2$ thin film formed by the sputtering method using the hydrofluoric acid type solution. Thus, while the plastic base plate holds the shape of the passage formed thereon, the measuring cell can be formed. Further, a hydrophobic problem on the surface, which can be seen on many plastic materials, can be solved by covering the inner surface of the passage groove 6 with the $SiO_2$ thin films having a hydrophilic property.

Hereinabove, while the embodiment of the present invention has been explained, the present invention is not limited thereto, and can be varied within the subject of the invention specified in the claims. For example, in case the base plates 1, 2 are made of a plastic material, when the plastic base plates are covered by the $SiO_2$ film, there has been often seen a poor adhesiveness between the $SiO_2$ films and the plastic base plates. In such a case, it is possible to improve the adhesiveness by applying a surface reforming agent, such as a silane coupling agent, to the plastic surfaces in advance.

The sectional shape of the passage groove 6 is not limited to the semi-oval as shown in FIG. 2(d). For example, in case the process shown in FIG. 2(c) is carried out by etching using a gas, such as $CF_4$, $C_2F_2$, $CHCF_3$ or a mixture thereof, the section of the passage groove 6 becomes a rectangular shape.

Also, the material of the base plates 1, 2 can be selected in accordance with a wavelength of a measuring light to be used. For example, in case a visible light is applied, PYREX GLASS may be used. In case a light of an ultraviolet region is used, an ultraviolet transparent glass base plate, such as UV-22 produced by HOYA Corporation or #9741 produced by Corning Inc., having a good transmittance to the ultraviolet region, or the quartz glass through which the ultraviolet rays substantially completely pass has to be used as the base plate material. In case the base plate materials other than the quartz glass are used, approximately the same manufacturing process as that employed in the present embodiment is applied thereto.

According to the measuring cell of the present invention, since a portion of the passage groove, which has the fine width and depth highly accurately formed by the photo-fabrication technique and wet-etching technique and which has the same sectional area of the passage as that of a separation capillary column, is used as a measuring chamber, a measuring chamber having a fine volume which does not impair separating in analyzing abilities of various separation analyzing devices can be obtained. Also, when the two glass base plates are joined together, the joining interfaces or surfaces are covered by the $SiO_2$ films formed by the sputtering method so that distortions and thermal stress are not formed on the base plates to thereby obtain a reliable joining. Further, a measuring cell having various physical and chemical characteristics can be relatively simply obtained by covering the inner surface of the passage with the films having different materials and manufacturing conditions.

Also, the thickness and characteristics of the $SiO_2$ film playing an important role in joining the two base plates can be easily controlled by the film forming conditions to thereby manufacture a reliable measuring cell. Further, since the measuring cell with slits for shutting out the incident lights other than the lights which pass through the liquid sample can be obtained, the stray lights entering the detecting device can be reduced and the detecting device measures only lights which interact with the sample to thereby improve the measuring sensitivity. Also, since the measuring cell of the present invention is manufactured by the semiconductor manufacturing technique, the whole measuring cell is miniaturized with high accuracy, so that a plurality of the measuring cells can be manufactured at the same time to thereby easily reduce the cost.

What is claimed is:

1. A measuring cell comprising:

two base plates having joining surfaces, silicon oxide films formed on the joining surfaces without using a thermal oxidation method so that the two base plates are joined together through the silicon oxide films, a sample introducing port for introducing a fluid sample formed in at least one of the base plates, a discharging port for discharging the fluid sample formed in at least one of the base plates away from the sample introducing port, a passage communicating between the sample introducing port and the discharge port for allowing the sample to flow therethrough and having as a part thereof a measuring chamber formed between the two base plates joined together, and a protective film formed on one of the base plates, said protective film covering the joining surfaces except for the passage to form a slit so that the joining surfaces are optically opaque and light as intended can pass only through the passage not covered by the protective film while preventing stray light from entering the passage.

2. A measuring cell as claimed in claim 1, wherein at least one of the base plates forming the measuring chamber is made of one of a plastic material and a glass material, and said base plates include surfaces constituting the sample introducing port, the passage and the discharge port, said surfaces being covered with the silicon oxide films same as those formed on the joining surfaces.

3. A measuring cell as claimed in claim 2, wherein said one of the base plates includes a groove portion for constituting the passage, and the other of the plates includes holes spaced apart from each other for constituting the introducing port and the discharge port.

4. A measuring cell as claimed in claim 3, wherein said protective film is formed between one of the two base plates and one of the silicon oxide films formed thereon.

* * * * *